(12) United States Patent
Schneiderman et al.

(10) Patent No.: US 11,141,261 B2
(45) Date of Patent: Oct. 12, 2021

(54) METHOD AND DEVICE FOR LOCALIZED INTRAVASCULAR THERAPY

(71) Applicants: Jacob Schneiderman, Kiryat Ono (IL); Moshik Cohen, Petah Tikva (IL)

(72) Inventors: Jacob Schneiderman, Kiryat Ono (IL); Moshik Cohen, Petah Tikva (IL)

(*) Notice: Subject to any disclaimer, the term of this patent is extended or adjusted under 35 U.S.C. 154(b) by 184 days.

(21) Appl. No.: 16/330,377

(22) PCT Filed: Sep. 5, 2017

(86) PCT No.: PCT/IL2017/050998
§ 371 (c)(1),
(2) Date: Mar. 5, 2019

(87) PCT Pub. No.: WO2018/042446
PCT Pub. Date: Mar. 8, 2018

(65) Prior Publication Data
US 2020/0375719 A1 Dec. 3, 2020

Related U.S. Application Data

(60) Provisional application No. 62/383,511, filed on Sep. 5, 2016.

(51) Int. Cl.
*A61F 2/06* (2013.01)
*A61M 25/00* (2006.01)
*A61M 25/01* (2006.01)

(52) U.S. Cl.
CPC ........... *A61F 2/06* (2013.01); *A61M 25/0074* (2013.01); *A61F 2210/0004* (2013.01);
(Continued)

(58) Field of Classification Search
CPC ... A61B 5/0084; A61B 5/0086; A61B 5/6858; A61B 5/6876; A61B 2562/0233; A61F 2/06; A61F 2/07; A61F 2210/0004; A61F 2220/0016; A61F 2250/0068; A61F 2002/072; A61F 2002/075; A61F 2002/077; A61M 25/0074; A61M 25/04; A61M 2025/0024; A61M 2025/0057; A61M 2025/0166; A61M 29/00; A61M 2205/3317; A61M 25/10; A61M 25/1018; A61M 25/1084; A61M 25/10181;
(Continued)

(56) References Cited

U.S. PATENT DOCUMENTS 6,245,026 B1 6/2001 Campbell et al.
8,968,390 B2 3/2015 Richter
(Continued)

*Primary Examiner* — Kami A Bosworth
(74) *Attorney, Agent, or Firm* — Soroker Agmon Nordman

(57) ABSTRACT

A non-occlusive intravascular device for local application of a therapeutic agent to a selected segment of a lumenal wall of a blood vessel without applying radial force on the wall. The device comprises a radially expandable/collapsible flexible scaffold of an open-skeletal structure and a flexible outer surface capable of conforming to the lumenal wall without applying radial force thereon and a controllable mechanism for expanding and collapsing the scaffold. The therapeutic agent is loaded and carried on the outer surface of the scaffold. Also provided are a method and a system for delivering a therapeutic agent to a selected segment within a blood vessel.

15 Claims, 5 Drawing Sheets

(52) U.S. Cl.
CPC .......... *A61F 2220/0016* (2013.01); *A61F 2250/0068* (2013.01); *A61M 2025/0057* (2013.01); *A61M 2025/0166* (2013.01); *A61M 2205/3317* (2013.01)

(58) Field of Classification Search
CPC ...... A61M 25/10187; A61M 25/10188; A61M 25/104; A61M 25/105; A61M 2025/102; A61M 2025/1022; A61M 2025/1047; A61M 2025/1095; A61M 2025/1097; A61N 1/30; A61N 1/306
See application file for complete search history.

(56) References Cited

U.S. PATENT DOCUMENTS

| | | | | |
|---|---|---|---|---|
| 2004/0267355 | A1* | 12/2004 | Scott | A61M 29/02 623/1.42 |
| 2005/0107738 | A1* | 5/2005 | Slater | A61M 25/10 604/96.01 |
| 2009/0076448 | A1* | 3/2009 | Consigny | A61B 17/22 604/103.01 |
| 2009/0270787 | A1 | 10/2009 | Oepen et al. | |
| 2010/0163023 | A1* | 7/2010 | Singh | A61M 16/0438 128/200.26 |
| 2010/0222786 | A1* | 9/2010 | Kassab | A61B 5/01 606/127 |
| 2011/0022026 | A1* | 1/2011 | Sorensen | A61L 31/148 604/507 |
| 2011/0137155 | A1 | 6/2011 | Weber et al. | |
| 2012/0289982 | A1* | 11/2012 | Gunday | A61M 25/10 606/159 |
| 2013/0282084 | A1 | 10/2013 | Mathur et al. | |
| 2014/0012160 | A1* | 1/2014 | Ghaffari | A61B 5/6853 600/587 |
| 2015/0105715 | A1 | 4/2015 | Pikus et al. | |
| 2015/0223704 | A1* | 8/2015 | Haverkost | A61B 5/6856 600/481 |
| 2015/0238144 | A1* | 8/2015 | Pintel | A61B 5/6885 600/593 |

* cited by examiner

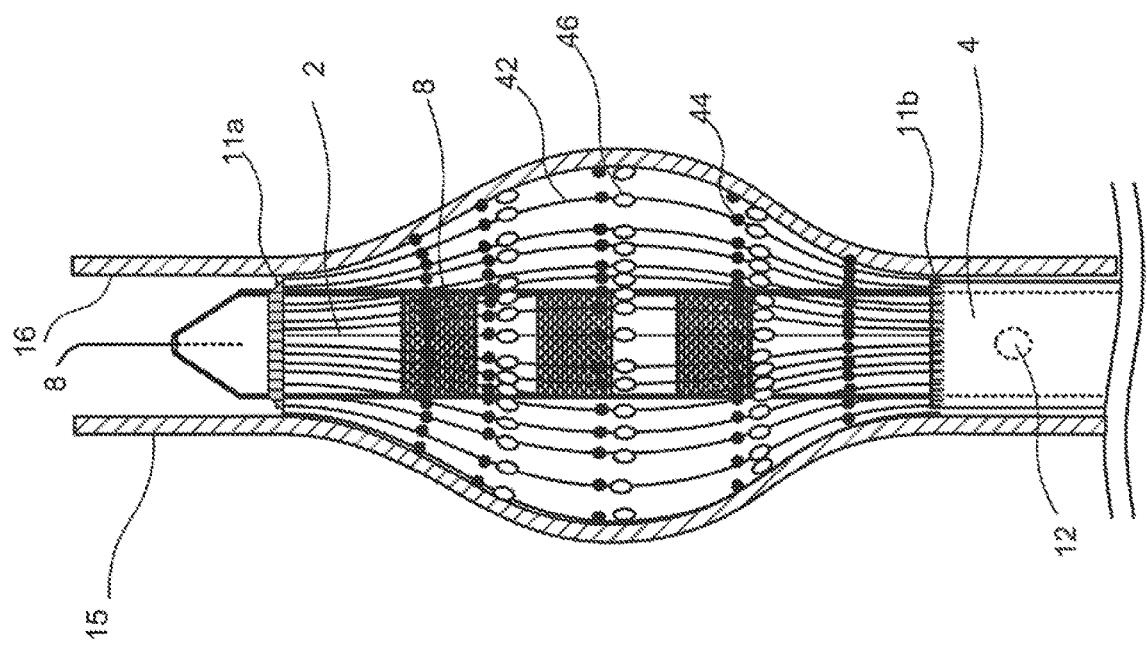
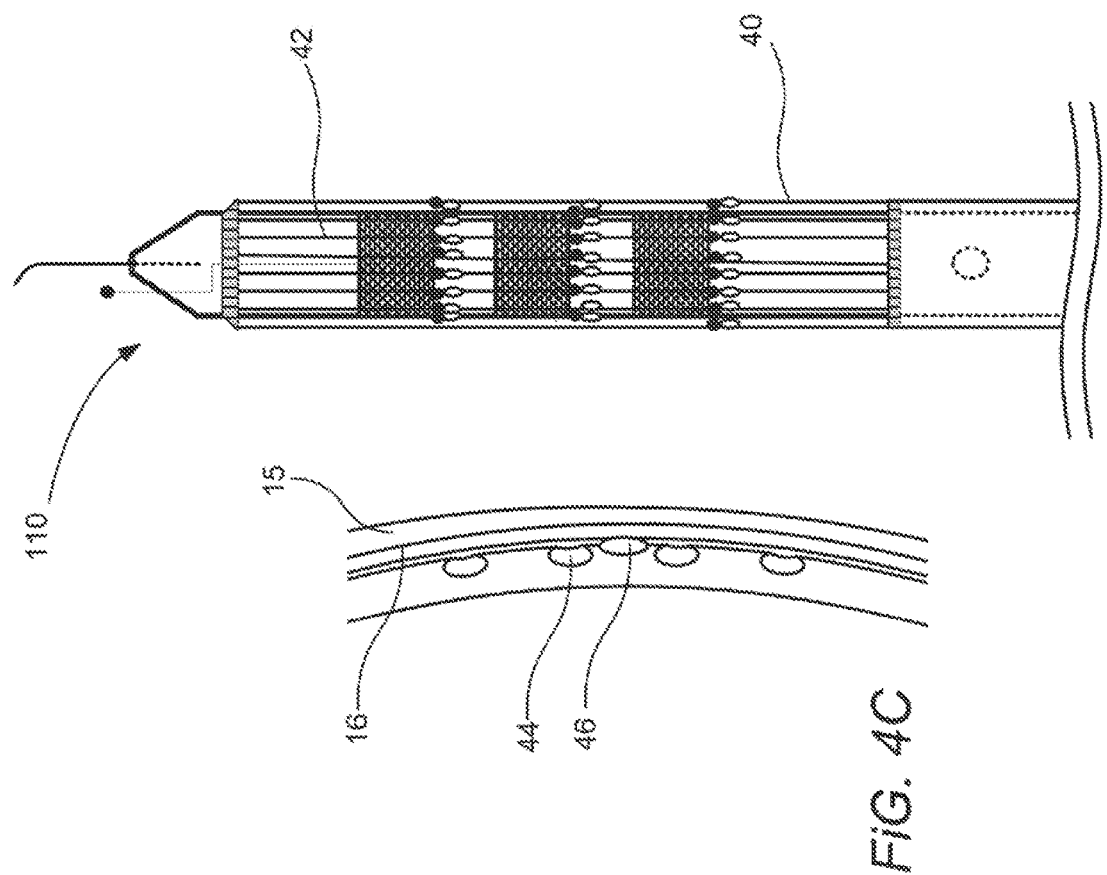

METHOD AND DEVICE FOR LOCALIZED INTRAVASCULAR THERAPY

FIELD OF THE INVENTION

The present invention generally relates to medical devices and to methods of treatment using such devices. More specifically, the invention relates to intravascular devices for local therapy of a selected site in a blood vessel, suitable for, but not limited to, the treatment of aneurysms.

BACKGROUND OF THE INVENTION

Aortic aneurysm (AA) is an enlargement (dilation) of the aorta, which is caused by weakening of the aortic wall presenting a risk of aortic rupture. When rupture occurs, it results with massive internal bleeding and, unless treated immediately, shock and death are inevitable.

Aortic aneurysms are age related, involving 5-9% of all males over 65 years of age. Expenditure on therapies related to AA exceeds $50 billion in the US, annually. Current treatments for sizable AA include endovascular implantation of intra-aortic stent graft, or open aortic surgery. Thus, an arrest of AA progression at early stage, or significant attenuation of AA expansion, is likely to revolutionize the mode of treatment, decrease the rate of related complications, and cut the cost of treatment, worldwide. This objective may be achieved for example, by introducing a therapeutic agent, e.g., a leptin antagonist or a matrix metalloproteinase (MMP) inhibitor, to the lumenal wall at the site of aneurysm to inhibit local processes of tissue degeneration, or alternatively by localized modulation of gene expression in the vessel wall, to achieve a similar end.

Drug coated eluting inflatable balloons are known for local delivery of drug into a cardiovascular tissue. Such balloons are currently used to open narrowed vessels (i.e., stenosis) and/or to prevent re-stenosis. However, these balloons are designed with predetermined dimensions and achieve attachment to the lumenal wall through forceful, uncontrolled balloon inflation. As such, they do not fit to deliver drug into a friable tissue, susceptible to rupture, such as in the case of aneurysm. Moreover, a major drawback associated with standard inflatable balloons is that most of them reduce or even totally occlude the blood flow in the treated vessel, causing distal ischemia and hemodynamic instability, thus limiting the available contact time with the blood vessel, and hence reduce the amount of drug that can be delivered, if tissue damage is to be avoided. Although non-occlusive inflatable balloons have been previously described, these balloons are also using pressurized fluid for their inflation and therefore do not fit for use for the treatment of weakened aneurismal vessels, as well.

There is therefore an ongoing need for new and improved intravascular methods and devices for local drug delivery into diseased vascular tissues, in particular for delivering drug into weakened and friable blood vessels, without applying radial force on the inner (lumenal) wall of the treated vessel and without disrupting the blood flow during the procedure.

Accordingly, the present invention is generally aimed at providing devices and methods for intravascular therapy of vascular disorders by local delivery of a therapeutic agent to a selected site within a lumen.

A further objective of the invention is to provide intravascular devices and methods for the treatment of aneurysm by delivering a therapeutic agent to the aneurysmal site, preferably at an early stage following diagnosis, so as to prevent or attenuate progression of a pre-existing aneurysm.

In particular, it is an objective of the invention to provide intravascular devices that can be used for local delivery of a therapeutic agent to a lumenal site where the vessel wall is friable, inflamed, or prone to rupture as in aneurysm, without applying radial force against the vulnerable wall.

Yet, a further object of the invention is to provide intravascular devices for local delivery of a therapeutic agent to a selected site of a lumen without interfering with the blood flow within the blood vessel.

SUMMARY OF THE INVENTION

According to some embodiments of the invention, an over-the-wire non-occlusive intravascular catheter designed to deploy local therapy to an artery or vein at a selected location, is disclosed. The intravascular catheter or device includes a scaffold coupled to its distal end, capable of controlled widening within the lumen of an aneurysm or any selected vascular segment. This scaffold when folded is loaded to carry (for example) an expandable, detachable biodegradable slow release drug constructed as a film, mesh, net, or stent, biodegradable construct containing drug encapsulated in nanoparticle vesicles (pre-loaded prior to catheterization), or alternatively a matrix carrying a vector for localized gene modulation. Such drug carrying construct or vector may be loaded onto the folded scaffold and may be configured to detach at the lumenal surface in order to achieve a specific localized therapeutic effect.

The scaffold is driven to expand and widen in a controlled manner, thus to gently attach to the inner surface of the vessel. The scaffold is configured to accommodate itself against the contour of the lumenal surface of the vessel at a desired location, without applying any radial force locally e.g., unlike an inflation of a balloon. Routine balloon assisted deployment requires its inflation by applying fluid pressure of a few atmospheres. However, this pressure applied against a weakened vessel wall may cause rupture thereof. A no-pressure contact is achieved through a built-in system that detects contact and prevents any further undesired expansion of the scaffold. This system may be operated by electromagnetic sensing. This unique property makes it especially suitable for vascular aneurysms, or severely inflamed arteries, where any application of radial force against the vessel wall is contraindicated.

The scaffold device does not interfere with free blood flow within the treated vessel throughout the process of its expansion, including its final position or final state, when fully approximated against the lumenal wall, or by the low profile of the detached construct.

The device carries optical antennas arranged along its main stem or longitudinal axis, providing capabilities to generate an electromagnetic radiation field locally at the designated vessel area. Generation of a local electromagnetic field may be advantageous when using biodegradable slow release therapeutic film, which contains, for example, an active agonist incarcerated within nanoparticles. The electromagnetic field may induce disintegration of nanoparticle vesicles, thereby causing release of the therapeutic agent making it available to contact the lumenal wall. In some embodiments, these optical antennas may alternatively emit light (at different wavelengths, at varying intensities) to activate crosslinking of matrix components to the lumenal wall, thereby causing fusion of a drug releasing biodegradable mesh carried by the scaffold to the lumenal wall. Additionally, the optical antennas may be utilized in order to determine or assess the distance between the scaffold and the inner aspect of the lumenal wall.

One aspect of the invention is a non-occlusive intravascular device for local application of a therapeutic agent to a lumenal wall of a blood vessel at a selected site within the vessel, the device comprising: a catheter having a distal end and a proximal end; a radially expandable/collapsible flexible scaffold circumferentially connected around a distal portion of said catheter extending between a first location and a second location on the distal portion, wherein said scaffold has an open-skeletal structure and a flexible outer surface capable of conforming to the lumenal wall at the selected site without applying a force thereon and wherein said therapeutic agent is carried on the outer surface of the scaffold. The device further comprises a controllable mechanism for expanding and collapsing the scaffold; one or more electromagnetic transmitters located on the catheter between the first and the second locations; and a plurality of touch sensors distributed at key points on the outer surface of said scaffold. In a full collapsed state the scaffold assumes a tubular form. The electromagnetic transmitters and the touch sensors are in a communication with a controller.

In accordance with certain embodiments of the catheter comprises a first shaft and a second shaft, each having a respective distal end and a respective proximal end wherein the second shaft is slidably mounted around the first shaft, wherein the scaffold has one end circumferentially coupled to the distal end of the first shaft and a second opposite end circumferentially coupled to the distal end of the second shaft and wherein the controllable mechanism comprises a driving means for moving said second shaft along said first shaft, thereby expanding and collapsing the scaffold.

The scaffold may comprise a flexible net or can comprise a plurality of flexible longitudinal wires.

In accordance with certain embodiments, the scaffold carries on the outer surface thereof a biodegradable construct comprising said therapeutic agent in a slow-release formulation. The biodegradable construct may be selected from the group consisting of a mesh, a film, a stent, a net and a thread. Yet, according the wires constituting the scaffold may comprise a plurality of outer surface reservoirs containing the therapeutic agent, preferably formulated to form encapsulated nanoparticles.

A further aspect of the invention is a method for delivering a therapeutic agent to a selected site in a lumenal surface of a blood vessel, the method comprising: advancing the intravascular device of the invention to the selected site, expanding the scaffold to obtain contact with and conformation of the scaffold to the lumenal surface at the selected site; and facilitating introduction of the therapeutic agent to the lumenal surface.

Yet a further aspect of the invention is a system for delivering a therapeutic agent to a lumenal site, the system comprising the intravascular device of the invention, a light source and control unit comprising a processor in communication with the controllable mechanism, the touch sensors, the electromagnetic transmitter and the light source. The controller is programmed to collect data from the touch sensors and the optical antenna, to process the data and to control the operation of the device in accordance with the processed data.

The intravascular devices described herein can also be referred to interchangeably as "catheters".

BRIEF DESCRIPTION OF THE FIGURES

The present invention will be understood and appreciated more fully from the following detailed description taken in conjunction with the drawings in which:

FIGS. 4A, 4B and 4C are a schematic illustrations of a further embodiment of the intravascular device of the invention, showing a different version of the scaffold in collapsed state, in an expanded state within a blood vessel, and a detail of a wire comprising the scaffold, respectively;

DETAILED DESCRIPTION OF THE PREFERRED EMBODIMENTS

Figure 1:
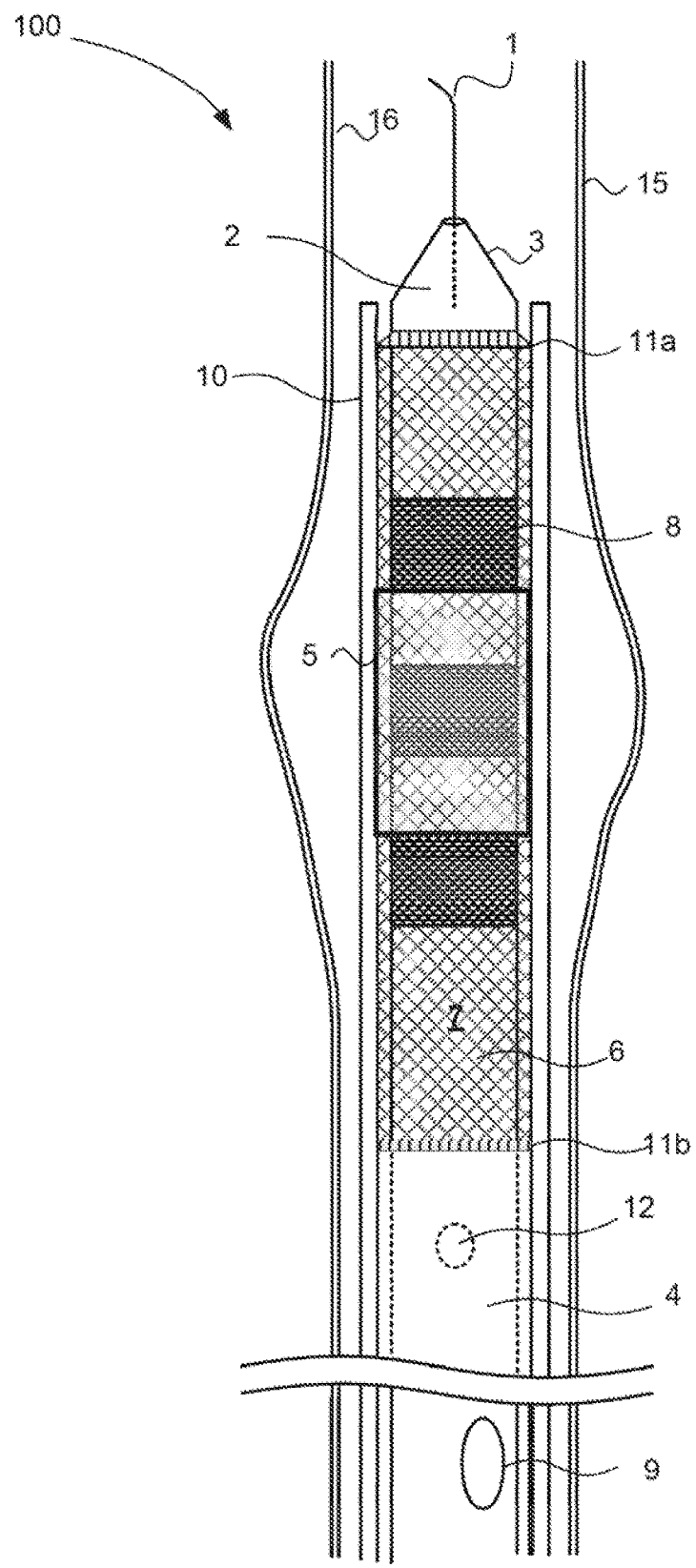
FIG. 1 is a schematic illustration of an intravascular device in accordance with an embodiment of the present invention, positioned within an aneurysmal lumen.

There is provided a minimally-invasive, non-occlusive, intravascular device that is designed for delivering a therapeutic agent to a selected site within a blood vessel (arteries and veins) in order to achieve a localized therapeutic effect without producing undesired systemic side effects. The device is specifically suitable for, but is not limited to, lumenal application within blood vessels having weakened and friable walls, like an aneurysm or a vessel involved in local inflammation (arteritis etc.). The vessel may be, for example, the aorta or a peripheral artery affected by aneurysmal changes or local inflammation.

The key advantages of the intravascular device of the invention are conformation to the lumenal wall for localized delivery of the therapeutic agent without applying any radial force locally, the ability to promote fusion of the therapeutic agent to the lumenal surface of the vessel, and being non-occlusive to blood flow within the treated vessel. Other advantages of the invention will be apparent from description which follows.

The intravascular device of the invention comprises at the distal part thereof a radially expandable and collapsible scaffold that carries the therapeutic agent on the outer surface. The scaffold comprises wires of flexible material which lay flat against the catheter shaft when the scaffold is in a collapsed state and form a hollow flexible skeletal 3D structure when the scaffold is expanded, allowing blood to flow in between the wires. The flexibility of the skeletal structure allows the scaffold to easily conform to the lumenal surface without applying a force thereon, thus providing optimal attachment for effective drug delivery. In accordance with certain embodiments of the invention the scaffold wires are formed as a net. According to other embodiments, the scaffold comprises only longitudinal wires. In either case, the opposite free ends of the wires are circumferentially coupled to the catheter shaft.

In accordance with certain embodiments of the invention, the scaffold comprises a plurality touch sensors, distributed at key points on the outer surface thereof, in communication with a control unit. The touch sensors are designed to detect minimal contact with the lumenal surface. A control unit processes the data received from the multiple sensors and provides an indication when optimized deployment of the scaffold is achieved.

In accordance with certain embodiments of the invention, the scaffold carries on its outer surface a biodegradable film-like construct which contains the therapeutic agent, which construct is attached to the lumenal surface of the treated vessel upon the scaffold expansion and fused thereon for slow release of the agent into the lumenal tissue. In accordance with other embodiments of the invention, the scaffold carries reservoirs of the therapeutic agent, preferably in the form of encapsulated particles (e.g., nanocapsules)

In accordance with certain embodiments of the invention, the intravascular device comprises means for attaching the biodegradable film-like construct or for releasing the therapeutic agent from the reservoirs into the lumenal surface. In accordance with certain embodiments of the invention, the means comprises electromagnetic irradiation means.

Referring to the figures, FIG. 1 schematically illustrates an intravascular device in accordance with an embodiment of the invention. The device, generally designated 100, is an intravascular catheter configured to slide over the guide-wire 1 inside blood vessel 15, as is well known in the art. Device 100 comprises a main tubular central elongate shaft 2 and an overriding tubular shaft 4 which is telescopically mounted around shaft 2, allowing reciprocal linear movement of shaft 4 along shaft 2. Both members 2 and 4 are made of a flexible material to allow navigation to the site of treatment, as is well known in the art. Catheter 100 further comprises at its distal end a therapeutic agent delivering device in the form of an expandable/collapsible scaffold 6 which is coupled to and extends between the distal ends of shafts 2 and 4, 11a and 11b, respectively. In accordance with the embodiment shown here, scaffold 6 is shaped as a net 7 having one end circumferentially coupled to shaft 2 and the opposite end circumferentially coupled to shaft 4. Scaffold 6 may be attached to shaft 2 a few centimeters proximally to conic tip 3 and in its collapsed flattened state may extend to about 1.2-12 centimeters. Scaffold 6 can be coupled to the shafts by any suitable connection or attaching means, including, but not limited to, welding, soldering biocompatible gluing and mechanical connection means.

The design of scaffold 6 allows for loading an expandable, biodegradable slow release film-like construct 5, which is pre-loaded with a therapeutic agent, on top of the unexpanded (collapsed) scaffold, around the middle portion thereof. Construct 5 may be a mesh, a film, a stent, a net, a thread, or a matrix for vector transfer, destined for gene modulation to be applied to the lumenal vessel wall when expansion process is complete. Examples for biodegradable polymers that may be used in the fabrication of construct 5 include polyglycolic acid (PLGA), hydrogel, polylactic acid, polysaccharides and resins. Construct 5 may have a rough surface or miniature hooks to anchor into the lumenal surface. In some embodiments, the construct 5 may include a drug eluting mesh configured to enable slow release of a first drug into the wall of the vessel, and/or in addition may be configured to enable slow release of a second drug or composition into the lumen, to be carried by the blood stream. For example, the mesh can be configured to release an anti-inflammatory drug, into the wall of the vessel and to release an anticoagulant, e.g., heparin, to the lumen.

It will be realized that moving shaft 4 linearly along shaft 2 towards tip 3 brings the opposite ends of scaffold 6 closer together, causing expansion (widening) of the scaffold, while moving shaft 4 in the opposite direction linear will cause scaffold 6 to collapse back to a flattened state. In accordance with certain embodiments of the invention, shaft 4 is coupled to a motor (not shown), e.g., a motion control electric servo motor, that drives the shaft 4 to controllably move along inner shaft 2, thereby allowing expansion and widening of scaffold 6 as well as later back-folding the scaffold when the add-on biodegradable construct 5 has been deployed to the lumenal surface. The motor may be constructed within shaft 4. The motor may be a miniaturized, high energy efficiency motor constructed within the main body of shaft 2. In accordance with other embodiments shaft 4 may be coupled to shaft 2 through a connecting means, e.g., a corkscrew mechanism.

It will be appreciated that due to the open-skeleton structure of scaffold 6 and the very slim profile of the wires forming net 7, as well as of that of construct 5, scaffold 6 when expanded to contact lumenal surface of 16 of blood vessel 15, does not interfere with blood flowing through the vessel. It will be also appreciated that net 7 may be designed to have larger openings both proximally and distally to further enhance free flow of blood.

Scaffold 2 is fabricated from a biocompatible non-degradable flexible material that is sufficiently flexible to enable the scaffold to conform to the contour of the inner surface of the vessel wall without exerting radial force thereon but that possesses sufficient stiffness to withstand the blood flowing in the vessel without deforming. The material can be any resilient biocompatible material including, but not limited to, polymer, synthetic rubber, natural rubber, silicone, metal, alloy, plastic, composite material or any combination thereof, selected to achieve suitable flexibility stiffness necessary flexibility and stiffness. For example, the strands comprising the scaffold may be made of metal alloys, such as nitinol (nickel/titanium alloy) or cobalt-chromium, or from polymers, e.g., a thermoplastic vulcanizate such as Santoprene™, that also might have some elasticity.

Catheter 100 also comprises a light source 12, e.g., laser, and optical antennas 8 arranged circumferentially along shaft 2, three according to the embodiment shown here, though in other embodiments, any other number of optical antennas may be incorporated as part of the intravascular scaffold device. Optical antennas 8 are used to generate light/electromagnetic field to promote fusion of the biodegradable construct 5 into the lumenal aspect 16 of the vessel, Antennas 8 may also be used to estimate the distance between scaffold 6 and lumenal wall 15, as explained in more detail below. Catheter 100 further comprises a plurality of touch or contact sensors (not shown) distributed at key points on net 7 configured to detect minimal contact levels with the lumenal surface, and an indicator 9, e.g. a light indicator, configured to signal adequate contact of scaffold 6 with lumenal surface 16, which in accordance to the embodiment shown here is positioned at the proximal end of the catheter. In other embodiments of the invention, the indicator may be positioned in an external unit, e.g., in a doctor interface module (see FIG. 5), to signal adequate contact of scaffold 6 with the lumenal surface 16. The touch sensors may be capacitive sensors or resistive sensors or may be designed to measure both capacitance and resistance. A retractable cover sheath 10 is used for smooth the introduction and retrieval of the catheter. Cover sheath 10 is withdrawn backwards to allow operating the catheter, and may be repositioned forward before removal of the catheter from the vascular system.

Figure 2A:
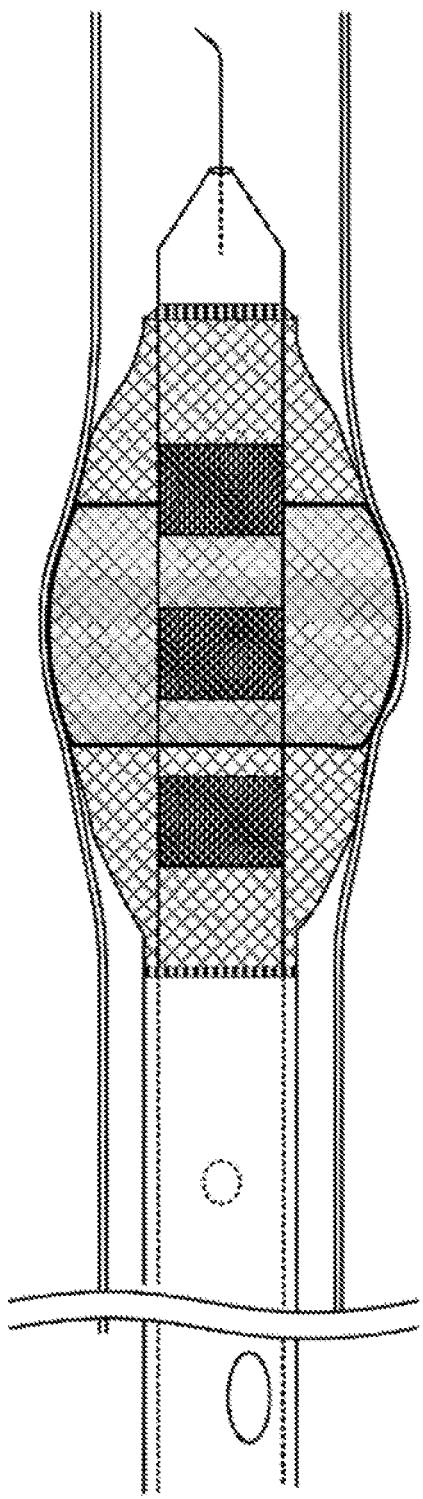
FIGS. 2A and 2B are schematic illustrations of the intravascular device of FIG. 1, in a deployed expanded state and back in a collapsed state before withdrawal, respectively.
Figure 2B:
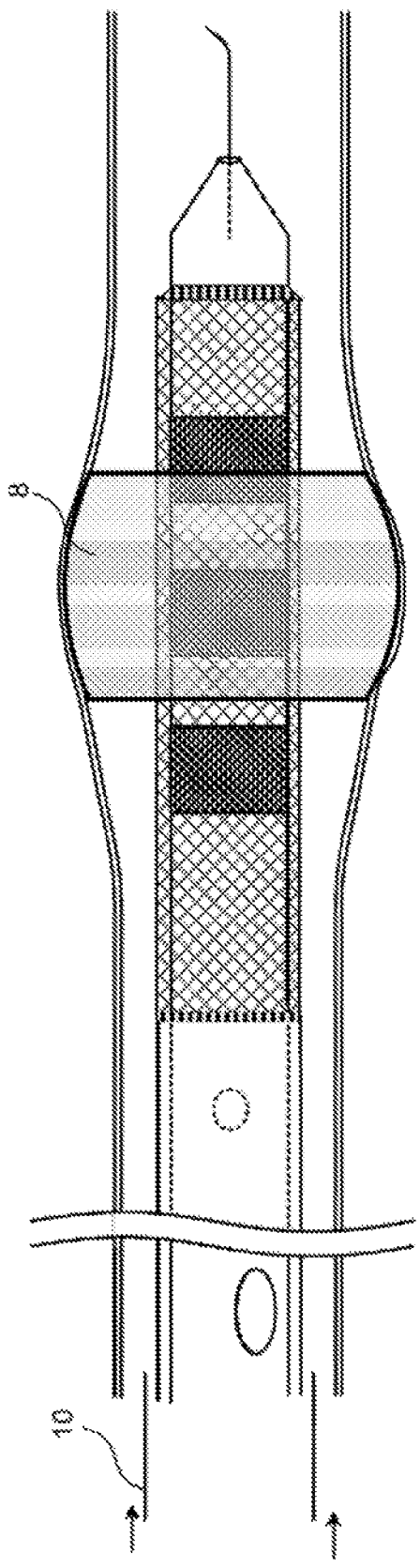

In use, catheter 100 (which has been pre-loaded with therapeutic construct 5 destined for the lumenal wall) is introduced, into the vascular system, e.g. via femoral catheterization, and is advanced over wire 1, fluoroscopy assisted, to be positioned in the aortic segment designed for treatment. The catheter can be introduced both via centrifugal or centripetal approach. Cover sheath 10 is withdrawn and after fine positioning adjustment within the dilated aortic segment, expansion of the scaffold 2 can be activated. In accordance with certain embodiments of the invention, net 7 may carry multiple opaque markers (not shown) to verify accurate positioning of scaffold 6. Expansion of scaffold 6 is activated by advancing shaft 4 towards tip 3, resulting in scaffold 6 assuming a widened middle section (e.g., "bulging belly"). Expansion of scaffold 6 continues under the control of a control unit (see Fig. X) that process the data received from the touch sensors and/or the optical antennas until scaffold 6 is fully engaged within the lumen of the diseased segment, as indicated by indicator 9, and biodegradable construct 5 may be attached to lumenal surface 16 (FIGS. 2A and 2B). A selected mode of optical antennas 8 is switched on to emit light or generate an electromagnetic field in order to achieve fusion of the biodegradable construct 5 to the wall. As shown in FIG. 2B, when attachment of construct 5 to lumenal surface 1 is complete, scaffold 6 is folded back and the cover sheath 10 is advanced forward to cover and contain the active part of the catheter. The catheter is now ready for complete smooth withdrawal from the vascular system. The arterial puncture site is closed, for example using a routine closing device. It is noted that when the therapeutic agent is formulated as nanoparticles, antennas 8 are also used for emitting electromagnetic radiation selected to facilitate disintegration of the particles and for introducing the therapeutic agent into the lumenal wall.

FIG. 4 schematically depict an alternative embodiment of an intravascular device, generally designated 110, according to which the expandable/collapsible scaffold, designated 40, has a corona-like structure, comprising a plurality of parallel flexible wires 42. Wires 42 are extending between the distal ends of shaft 2 and 4, circumferentially coupled thereto. Further in accordance with this embodiment wires 42 are provided with pits 44, which open to the outer surface of the wire facing the lumenal surface 16 to abut the vessel wall when scaffold 40 is fully deployed. Pits 44 serve as reservoirs of therapeutic agent, preferably formulated as nanoparticles. It will be realized that the number of wires 42 and the distribution and size of pits 44 along a wire as depicted in the figure is only for demonstration sake and that both the number of wires and the number of pits along each wire are typically much larger than depicted while the size of the pits is much smaller with respect to the wire length. Wires 42 are also provided with contact touch sensors 46, arranged in proximal, middle and distal rows. It will be realized that according to other embodiment the distribution of the touch sensors on the outer surface of the scaffold may assume different arrangements. In accordance with the embodiment shown here, antennas 8 emit electromagnetic radiation selected to facilitate disintegration of the particles and for introducing the therapeutic agent into the lumenal wall. In accordance with certain embodiments, wires 42 are fabricated from nitinol, or a material comprising nitinol, the diameter of the wires is in the range of 50-500 μM diameter, the wires are spaced apart by 100-500 μM in coupling regions 11a and 11b and pits 44 are 10-500 μm long.

Figure 5:
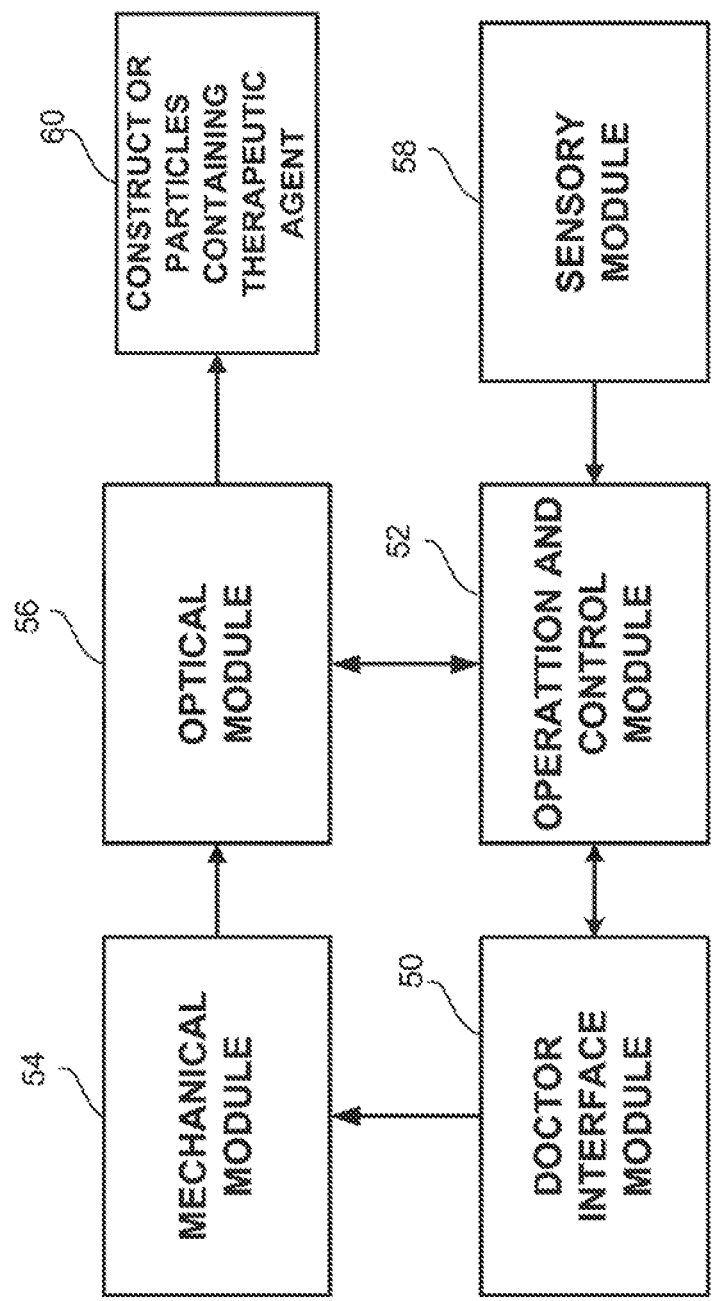
FIG. 5 is a functional block diagram of a system for delivery of a therapeutic agent to a lumen site, comprising the intravascular device of the invention.

The intravascular device of the invention operates under the control of a controller, that processes the data received from the touch and controls provides control of functions related to the scaffold device and to the optical antennas. FIG. 5 is an overall functional block diagram depicting the modules the system that includes the intravascular device and a controller. The system includes an operation and control module 52 in communication with mechanical module 54 for expanding and collapsing the scaffold, optical module 56 and a sensory module 58 which includes touch sensors 46.

Module 52 includes a controller, e.g., a microprocessor and a memory device, or a computer, and is preferably in communication with medical imaging system, e.g., a fluoroscopy apparatus, an ultrasound, MRI, etc. The system also includes a user (doctor) interface module which comprises a compact, portable console for remote control of the device operation, providing for automatic as well as manual operational modes. The console also provides for visual monitoring of adequate positioning and deployment of the scaffold, combined with imaging, angiography, ultrasound, or MRI.

Figure 3:
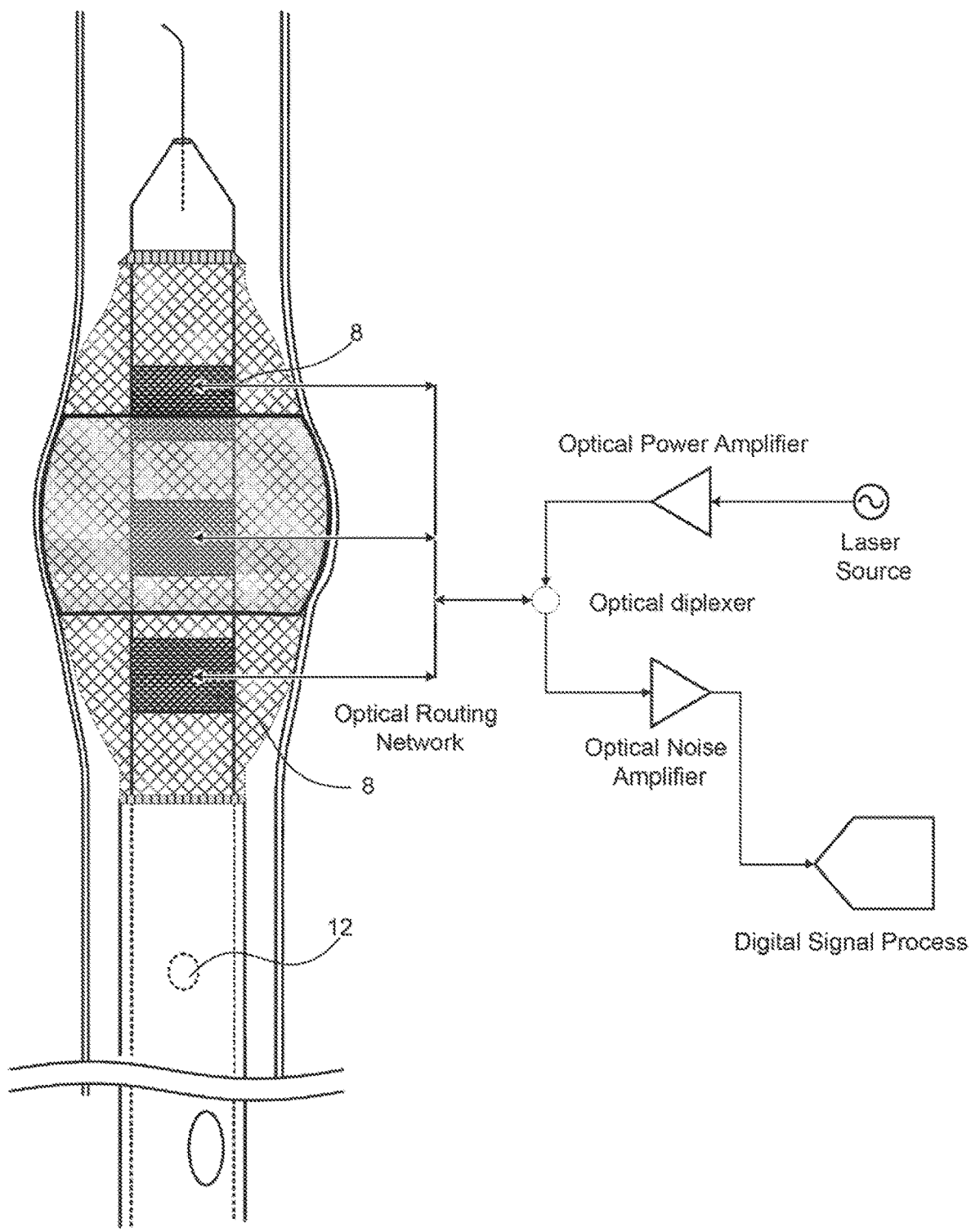
FIG. 3 depicts in a greater detail scaffold accommodated within an aneurysmal site and also diagrammatically illustrates the optical system coupled to the optical antennas located on the central catheter.

Referring to FIG. 3, the optical module 56 includes the light source 12 and the optical antennas 8 embedded within the intravascular device. The optical antennas may be made of metallic (e.g., Ag, Au, Al, etc.) or other composite material devices (e.g. polymers), which convert electromagnetic signals (e.g., photonic signals) propagating in waveguides (e.g. silicon photonics waveguides, plasmonic waveguides, dielectric waveguides, etc.) to free space optical radiation.

The optical antennas may be configured to operate in both transmission and reception modes, e.g. to simultaneously and/or intermittently transmit and receive signals. In transmission mode, the optical antennas convert the wave-guided signals that are required for contact detection (fanned scaffold against the lumenal vessel wall) and materials crosslinking into the actual radiation that performs theses interactions. In reception mode, the optical antennas collect the reflected radiation from the environment (e.g. blood, vessel wall, etc.), converted into the wave-guided signals that are being processed in the digital signal processing section. It is noted that the electromagnetic antennas, in some embodiments, may be electromagnetic antennas that transmit electromagnetic signals or radio waves.

The optical radiation transmitted by the optical antennas provides the required energy for the fusion of the biodegradable construct 5 (e.g. mesh, film or matrix) at the lumenal aspect to facilitate treatment of the vessel wall or for inducing disintegration of nanoparticle vesicles, thereby causing release of the therapeutic agent making it available to contact the lumenal wall.

The light radiation transmitted by the optical antennas is reflected from the lumenal wall and from the scaffold back to the optical antennas. The optical antennas also act as receivers, receiving the reflected light radiation and transferring these to the optical low noise amplifier for amplification. After amplifying the signals, an analog-to-digital unit converts the optical signals to digital signals which are processed by the processing unit to determine contact with the tissue or the lumenal vessel wall.

The optical diplexer acts as a signal routing unit—when detecting a signal that is received from the environment to the processing unit, it transfers the optical signals to the low noise amplifier, in the direction of the processing unit, without interference of other signals (e.g., the generated radiation or laser signals). When the optical diplexer detects signals that are transmitted from the radiation/laser source to the optical antennas, it routes the signals to the optical antennas for transmission of the light radiation to the lumenal vessel environment.

The controller may control at least one of frequency, waveform, intensity, phase and/or amplitude of the electromagnetic/light pulses or signals generated by the light source, controlling the modes and timing of the antennas states (transmission and reception).

A processing unit or Digital Signal Processor (DSP)—this is a digital computational unit, e.g. a processing unit or a computer, that is configured to perform the following functions:
 (I) conversion of optical signals into digital electrical signals
 (II) processing the digitalized signal and performing the required signal processing for contact detection
 (III) contact indication
 (IV) waveform generation for detection and tracking of required targets within the environment.

The processing unit is operationally connected to an optical low noise amplifier, an optical diplexer, an optical power amplifier and a signal source, e.g. a laser signal source. Electromagnetic Signal Source (e.g. optical signal source or laser source)—this is an electronic component that is responsible to electronically modulate the signal that is radiated by the laser source and optical antenna in transmitting mode. The signal source produces a modulated signal for best fit to the specific targets and environments within the defined system and scenarios. For example, the signal source will produce different waveforms for distance measurements of the fanning scaffold, other than those of the vessel wall. The signal source and/or laser source may also provide a range of various wavelengths 1. Contact Indication Module—this is an electro optic unit, assembled on the back side of the device, comprised of: (I) an electrical portion that continuously receives the information from the DSP and (II) light emitting diode (LED) which produces light upon predefined and configurable or programmable conditions.
2. Automatic Mode Selector—this is an electronic unit or integrated circuit (IC) that controls the transmission parameters of the laser (e.g., intensity and frequency) according to the sensor mode, in order to perform different operations (e.g. distance measurements, contact sensing & materials fusion)

In some embodiments, the system components may be included in a distal end of the intravascular catheter that carries the scaffold. For example, the antennas, signal source, controller and/or processing unit may be included in the distal tip of the catheter or arranged along a portion of its distal end. It is clarified that the distal end of the catheter is the portion of the catheter that enters the body and includes the tip of the catheter, e.g. the conic tip 3. The distal end is used to carry, for example, the scaffold and/or the mesh into the intravascular lumen. The proximal end of the catheter is the end that includes the actuating handle and/or catheter controller, and is not intended for entering the patient's body.

In some embodiments, e.g. in very narrow catheters required for entering into narrow arteries or veins, the system may include a portion of the components in a distal end of the catheter, while another portion of the components may be arranged remotely from the distal end, e.g. in the proximal end of the catheter or in an external unit coupled thereto.

For example, the antennas and/or optical transmitters/receivers or optical sensors may be embedded in the distal end of the catheter which is configured to enter the body, while other system components may be arranged in the proximal end of the catheter or in an external unit coupled thereto, e.g. located outside the body and not intended for in-vivo insertion. For example, an external unit positioned near the proximal end of the catheter, or coupled to the catheter, may include at least one of the following system components: laser source, controller, signal processing unit, optical power amplifier and/or optical low noise amplifier. The system components that are remote from the distal end of the catheter may be operationally connected, e.g. via wire connection and/or wireless connection, to the antennas or sensors or additional components that are embedded into or positioned within the distal end of the carrying catheter or near it. For example, wires may be woven through the catheter to deliver the optical signals received from the antennas in the distal end of the catheter to the external unit, and/or to transfer the signals generated by the laser source 12 from the external unit to the optical antennas/transmitters located at the distal end. Similarly, if the system components are positioned in the proximal end of the catheter, the signals may be transmitted to the distal end and from it using either wired or wireless communication.

The intravascular device of the invention may be utilized, for example, in the following clinical circumstances:
(a) in any aortic location or in a peripheral arterial segment prone to develop localized aneurysm
(b) in pre-existing aneurysms of the aorta, peripheral arterial or venous segments: mid-size arteries including the carotids, innominate, axillary, visceral, iliac, femoral, popliteal, etc.).
(c) in mid-size arteries involved in any type of arteritis, including Takayasu disease, etc.

The therapeutic agent delivered by the devices described herein can be any substance, including any drug, and the device can be used for local delivery of such substances to prevent or treat a variety of disease syndromes or to promote or enhance desired activity within the body. For example, the therapeutic agent may be an anti-inflammatory drug or an antiproliferative drug as those utilized in coronary drug eluting stents (DES). When the intravascular device of the invention is used for the treatment of aneurysm, the therapeutic agent may be a leptin antagonist or a matrix metalloproteinase (MMP) inhibitorm, for controlling medial degeneration, which underlies aneurysm progression. The therapeutic substance may also be an expression vector designed for introducing a modification into a target gene involved in the syndrome to be treated, by using the CRISPR Cas9 technology. For example, when directed at treating an aneurism, the therapeutic agent may a vector designed to decrease the production of leptin at an aneurismal site.

The intravascular devices of the invention can be designed in different sizes to fit the target blood vessel. It will be realized that also the particular design of the scaffold, i.e., material and structure (as well as dimensions), can be selected to best the vessel to be treated.

For example, Nitinol rods, may be most suitable for the device designed for intravascular local drug application in large vessels like the aorta (vessel's diameter 10-40 mm), while an expandable network made of cobalt-chromium may be preferable for local drug application for blood vessels of smaller diameter (2.5-5 mm).

It will be easily realized by persons skilled in the art that the embodiments described in the figures are only examples and that different features, which are described separately in conjunction with a particular embodiment, can be combined in the design of a device of the present invention. For example, the detachable film-like layer which is described in conjunction with a net-like scaffold can be combined with the scaffold structure illustrated with in FIG. 6. Much the same, the reservoirs illustrated in FIG. 6 can be combined with the net-like scaffold illustrated in FIGS. 1-3.

It will be appreciated by persons skilled in the art that the present invention is not limited to what has been particularly shown and described hereinabove. Rather the scope of the present invention is defined only by the claims which follow.

The invention claimed is:

1. A non-occlusive intravascular device for local application of a therapeutic agent to a lumenal wall of a blood vessel at a selected site within the vessel, the device comprising:
   a catheter having a distal end and a proximal end;
   a radially expandable/collapsible flexible scaffold circumferentially connected around a distal portion of said catheter extending between a first location and a second location on said distal portion, wherein said scaffold has an open-skeletal structure and a flexible outer surface capable of conforming to the lumenal wall at the selected site without applying a radial force thereon, and wherein said therapeutic agent is loaded on the outer surface of the scaffold;
   a controllable mechanism for expanding and collapsing said scaffold;
   a plurality of touch sensors distributed on the outer surface of said scaffold, configured to detect contact with the lumenal wall; and
   a control unit;
      wherein said touch sensors and said controllable mechanism are in communication with said control unit; and
      wherein said control unit is programmed to:
         collect and process data from the touch sensors;
         control expansion of said scaffold in accordance with the processed data; and
         prevent further expansion of the scaffold and provide an indication when optimized deployment of the scaffold is achieved.

2. The intravascular device of claim 1, wherein said catheter comprises a first shaft and a second shaft, each having a respective distal end and a respective proximal end and wherein said second shaft is slidably mounted around said first shaft;
   wherein said scaffold has one end circumferentially coupled to the distal end of the first shaft and a second opposite end circumferentially coupled to the distal end of the second shaft and wherein said controllable mechanism comprises a driving means for moving said second shaft along said first shaft, thereby expanding and collapsing said scaffold.

3. The intravascular device of claim 1, wherein said scaffold carries on the outer surface thereof a biodegradable construct comprising said therapeutic agent in a slow-release formulation.

4. The intravascular device of claim 3, wherein said biodegradable construct is selected from the group consisting of a mesh, a film, a stent, a net and a thread.

5. The intravascular device of claim 1, wherein said scaffold comprises a net.

6. The intravascular device of claim 1, wherein said scaffold comprises a plurality of longitudinal flexible wires.

7. The intravascular device of claim 6 wherein said wires comprise a plurality of outer surface reservoirs containing the therapeutic agent.

8. The intravascular device of claim 1, wherein said therapeutic agent is formulated in nanoparticles.

9. The intravascular device of claim 1, wherein said scaffold assumes a tubular form in a full collapsed state.

10. The intravascular device of claim 1, wherein said selected site is an aneurismal segment.

11. The intravascular device of claim 1, further comprising a light source and one or more optical antennas located on said catheter between said first and second locations.

12. The intravascular device according to claim 11, wherein said one or more optical antennas are in communication with said control unit and wherein said control unit is further programmed to collect data from said one or more optical antennas and to determine distance between the scaffold and the lumenal wall based on said data from said one or more optical antennas.

13. The intravascular device according to claim 12, wherein said scaffold carries on the outer surface thereof a biodegradable construct comprising said therapeutic agent in a slow-release formulation and wherein upon full deployment of the scaffold said one or more optical antennas are activated to emit light or generate an electromagnetic field in order to facilitate fusion of the biodegradable construct to the lumenal wall.

14. The intravascular device according to claim 12, wherein said therapeutic agent is formulated in nanoparticles and wherein upon full deployment of the scaffold said one or more optical antennas are activated to induce disintegration of said nanoparticles, thereby releasing the therapeutic to the lumenal wall.

15. A method for intravascular delivery of a therapeutic agent to a selected site in a lumenal surface of a blood vessel, the method comprising advancing the intravascular device of claim 1 to said selected site, expanding the scaffold to obtain contact with and conformation of the scaffold to the lumenal surface at said selected site and facilitating fusion of said therapeutic agent to the lumenal surface.

* * * * *